United States Patent [19]

Satoh et al.

[11] Patent Number: 4,861,908
[45] Date of Patent: Aug. 29, 1989

[54] ORGANOSILICON COMPOUND

[75] Inventors: Shinichi Satoh; Kazutoshi Fujioka, both of Annaka, Japan

[73] Assignee: Shin-Etsu Chemical Co., Ltd., Tokyo, Japan

[21] Appl. No.: 216,023

[22] Filed: Jul. 7, 1988

[30] Foreign Application Priority Data

Jul. 8, 1987 [JP] Japan .................. 62-170119

[51] Int. Cl.$^4$ ........................... C07F 7/10; C07F 7/18
[52] U.S. Cl. .................................................. 556/420
[58] Field of Search ........................................ 556/420

[56] References Cited

U.S. PATENT DOCUMENTS 4,048,207 9/1977 Jones ..................................... 556/420
4,509,816 4/1985 Newell et al. ........................ 556/420
4,697,026 9/1987 Lee et al. ......................... 556/420 X Primary Examiner—Paul F. Shaver Attorney, Agent, or Firm—Oblon, Spivak, McClelland, Maier & Neustadt

[57] ABSTRACT

An organosilicon compound represented by the general formula (I):

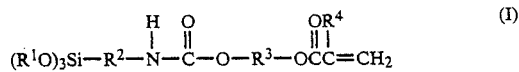

wherein $R^1$ may be the same or different and represents an alkyl group having 1 to 8 carbon atoms; $R^2$ and $R^3$ may be the same or different and represents an alkylene group having 1 to 8 carbon atoms; and $R^4$ represents a hydrogen atom or an alkyl group having 1 to 8 carbon atoms, and a process for preparing the same. This compound is useful for improving adhesive properties of UV curable silicone compositions and the like.

8 Claims, 5 Drawing Sheets

ORGANOSILICON COMPOUND

BACKGROUND OF THE INVENTION

1. Field of the Invention

This invention relates to an organosilicon compound, and particularly to an organosilicon compound useful for improving the adhesive properties of ultraviolet-curable silicone compositions or the like.

2. Description of the Prior Art

The organosilicon compound this invention provides is a hitherto unknown material.

SUMMARY OF THE INVENTION

An object of this invention is to provide a novel organosilicon compound that is useful for improving the adhesive properties of ultraviolet-curable silicone compositions or the like.

According to this invention, there is provided an organosilicon compound represented by the general formula (I):

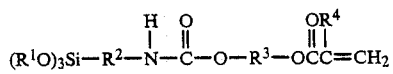
 (I)

wherein $R^1$ may be the same or different and represents an alkyl group having 1 to 8 carbon atoms; $R^2$ and $R^3$ may be the same or different and represents an alkylene group having 1 to 8 carbon atoms; and $R^4$ represents a hydrogen atom or an alkyl group having 1 to 8 carbon atoms.

The organosilicon compound this invention provides is a novel compound useful, for example, as an aid to improve adhesive properties of ultraviolet-curable silicone resins.

DETAILED DESCRIPTION OF THE INVENTION

Figure 1:
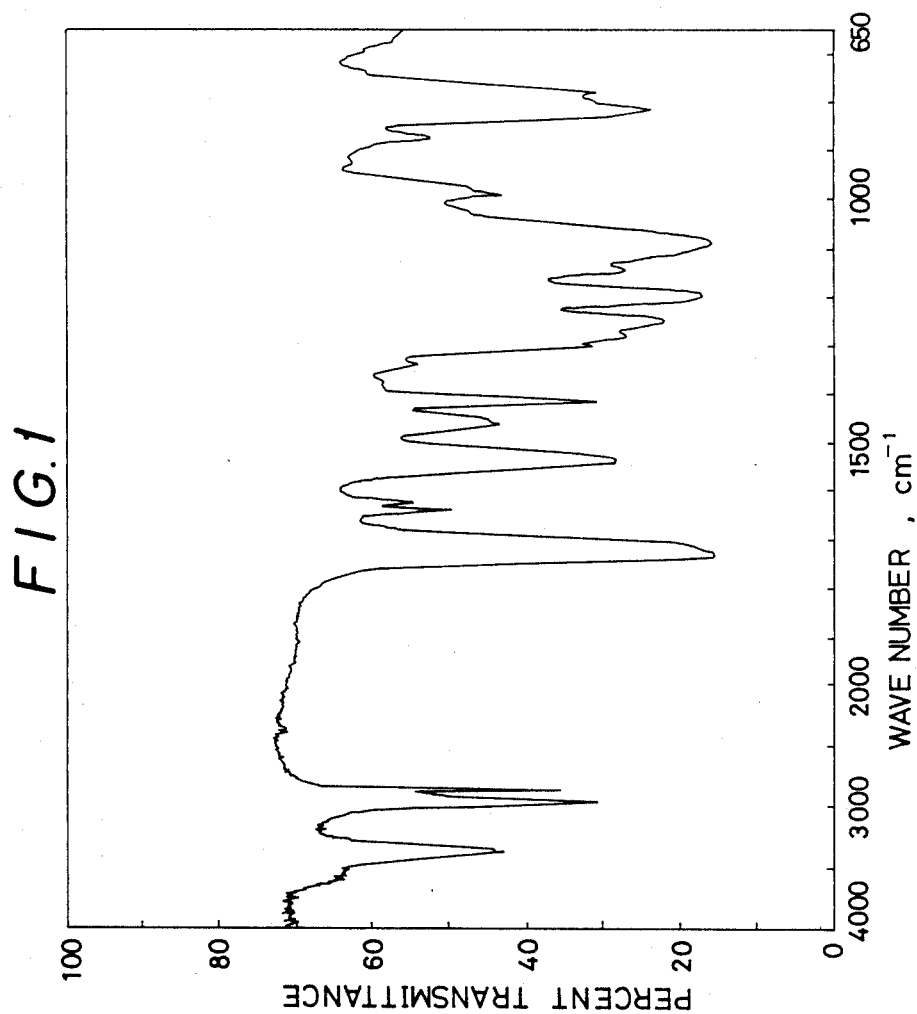
FIG. 1 to FIG. 5 show IR spectra of the organosilicon compounds of this invention obtained in Examples 1 to 5, respectively.

In the above the general formula (I), the alkyl group having 1 to 8 carbon atoms, represented by $R^1$ and $R^4$, may be straight or branched, including, for example, a methyl group, an ethyl group, a propyl group, an isopropyl group, a butyl group, a cyclopentyl group and a cyclohexyl group. The alkylene group having 1 to 8 carbon atoms, represented by $R^2$ and $R^3$, may be straight or branched, including, for example, $-CH_2-$, $-C_2H_4$, $-C_3H_6-$ and $-C_4H_8$.

The organosilicon compound of this invention can be synthesized by reacting an organosilicon compound represented by the general formula (II):

$$(R^1O)_3Si-R^2-N=C=O \qquad (II)$$

wherein $R^1$ and $R^2$ are as defined above; with a compound represented by the general formula (III):

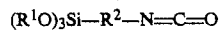
 (III)

wherein $R^3$ and $R^4$ are as defined above; in the presence of a catalyst. Useful as the catalyst in this reaction are, for example, organic tin compounds such as dibutyltin maleate, tributyltin acetate, dimethyltin dichloride, dibutyltin diacetate and dibutyltin dilaurate; and tertiary amines such as N-methylmorpholine, triethylamine, N-methylpiperidine, N,N-dimethylcyclohexylamine and pyridine, and they may preferably be added in an amount of from 0.001 to 1% by weight, particularly from 0.01 to 0.1% by weight, based on the organosilicon compound of the general formula (II). The reaction may preferably be carried out at a temperature of from 0° to 50° C., particularly from 20° to 40° C. The above reaction may usually be carried out without any solvent, but may be carried out using an organic solvent as exemplified by hexane, cyclohexane, benzene, toluene, xylene, tetrahydrofuran and acetonitrile, as required.

The thus obtainable organosilicon compound represented by the general formula (I) is useful as an improver for improving the adhesive properties of ultraviolet-curable silicone resins to substrates. For example, it may be added in the ultraviolet-curable silicone resin in an amount of from 0.01 to 1.0% by weight, whereby, after curing, the adhesion of the resin to substrates such as glass can be markedly improved.

This invention will be described below in greater detail by way of Examples.

EXAMPLES

Example 1

In a three-necked flask equipped with a reflux condenser and a thermometer, 10.3 g of 3-isocyanatopropyltrimethoxysilane, 5.8 g of 2-hydroxyethyl acrylate and 0.01 g of dibutyltin maleate were charged, and the contents were stirred for 8 hours at room temperature. The resulting reaction mixture in an amount of 150 mg was fractionated by gel permeation chromatography (GPC) to obtain 103 mg of a liquid product having a refractive index $n_D^{25}$ of 1.4544.

Next, this compound was subjected to measurement by GC-MS, $^1$H-NMR spectrometry, IR spectrophotometry and elementary analysis to obtain the results shown below.

GC-MS analysis: Parent ion peak, 321

NMR: δ (ppm): 0.52 (t, Si—CH$_2$, 2H), 1.55 (m, —C—CH$_2$—C, 2H), 3.05 (q, CH$_2$—N, 2H), 3.35 (s, Si—OCH$_3$, 9H), 4.18 (s, O—CH$_2$—CH$_2$—O, 4H), 5.12 (s, N—H, 1H), 5.5–6.3 (m,

3H).

IR spectrum: As shown in FIG. 1. Characteristic absorption bands (cm$^{-1}$) 3350 (N—H); 1726 (C=O); 1636, 1620 (C=C).

| Elementary analysis: (%) | | | |
|---|---|---|---|
| | C | H | Si |
| Calculated: (as C$_{12}$H$_{23}$NSiO$_7$) | 44.8 | 7.2 | 8.7 |
| Found: | 44.9 | 7.0 | 8.6 |

From the foregoing results, the above product was identified to be a compound represented by the formula:

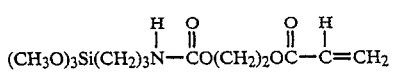

Yield: 69%.

Example 2

Example 1 was repeated except for using 6.8 g of 2-hydroxyethyl methacrylate in place of 2-hydroxyethyl acrylate, to obtain 112 mg of a liquid product having a refractive index $n_D^{25}$ of 1.4630.

Next, this compound was subjected to measurement by GC-MS, $^1$H-NMR spectrometry, IR spectrophotometry and elementary analysis to obtain the results shown below.

GC-MS analysis: Parent ion peak, 335

NMR: δ (ppm): 0.57 (t, Si—CH$_2$, 2H), 1.60 (m, C—CH$_2$—C, 2H), 1.93 (s, CH$_3$, 3H), 3.10 (q, N—CH$_2$, 2H), 3.56 (s, SiO—CH, 9H), 4.23 (s, O—CH$_2$CH$_2$—O, 4H), 5.43, 6.03 (s, C=CH$_2$, 2H).

Figure 2:
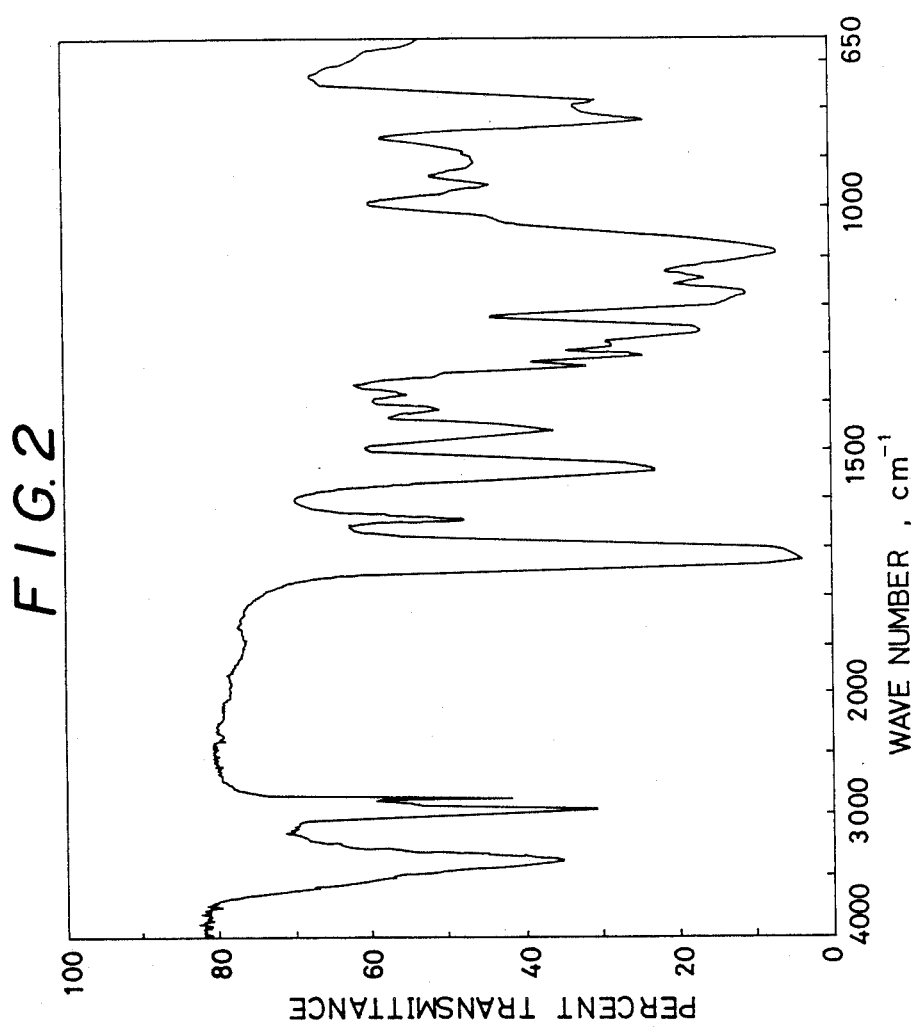

IR spectrum: As shown in FIG. 2. Characteristic absorption bands (cm$^{-1}$) 3350 (N—H); 1720 (C=O); 1637 (C=C).

| Elementary analysis: (%) | | | |
|---|---|---|---|
| | C | H | Si |
| Calculated: (as C$_{13}$H$_{25}$NSiO$_7$) | 46.6 | 7.5 | 8.4 |
| Found: | 46.5 | 7.4 | 8.3 |

From the foregoing results, the above product was identified to be a compound represented by the formula:

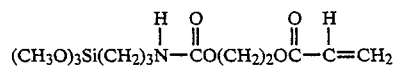

Yield: 76%.

Example 3

Example 1 was repeated except for using 6.2 g of 3-isocyanatopropyltriethoxysilane in place of 2-isocyanatopropyltrimethoxysilane and using 2-hydroxyethyl acrylate in a changed amount of 3.6 g, to obtain 97 mg (yield: 70%) of a liquid product having a refractive index $n_D^{25}$ of 1.4480.

Next, this compound was subjected to measurement by GC-MS, $^1$H-NMR spectrometry, IR spectrophotometry and elementary analysis to obtain the results shown below.

GC-MS analysis: Parent ion peak, 361.

NMR: δ (ppm): 0.54 (t, Si—CH$_2$, 2H), 1.19 (t, C—CH$_3$, 9H), 1.59 (m, C—CH$_2$—C, 2H), 3.09 (q, N—CH$_2$, 2H), 3.73 (q, O—CH$_2$, 6H), 4.12 (s, O—CH$_2$—CH$_2$—O, 4H) 5.6–6.3 (m,

3H.

Figure 3:
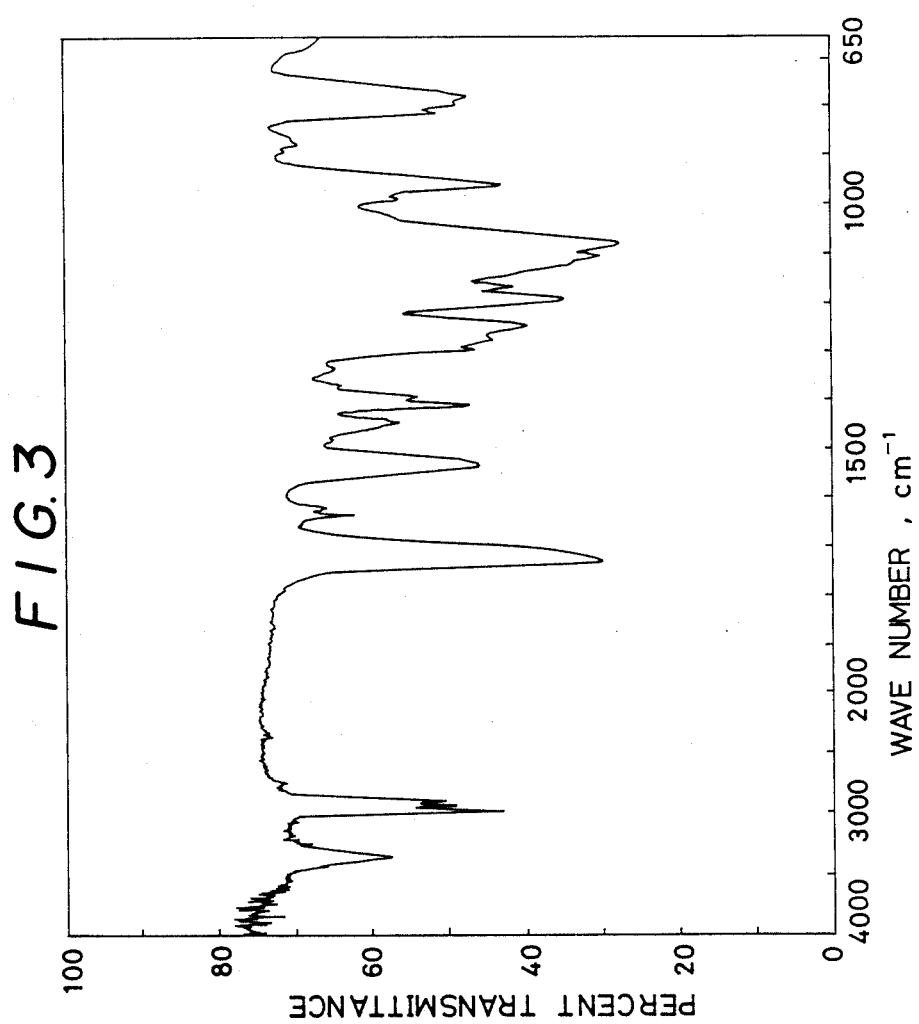

IR spectrum: As shown in FIG. 3. Characteristic absorption bands (cm$^{-1}$) 3350 (N—H); 1729 (C=O); 1636, 1620 (C=C).

| Elementary analysis: (%) | | | |
|---|---|---|---|
| | C | H | Si |
| Calculated: (as C$_{15}$H$_{44}$NSiO$_7$) | 49.6 | 8.0 | 7.7 |
| Found: | 49.7 | 8.0 | 7.8 |

From the foregoing results, the above product was identified to be a compound represented by the formula:

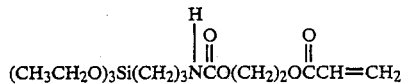

Yield: 70%.

Example 4

Example 1 was repeated except for using 7.8 g of 2-hydroxyisopropyl acrylate in place of 2-hydroxyethyl acrylate, to obtain 102 mg of a liquid product having a refractive index $n_D^{25}$ of 1.4512.

Next, this compound was subjected to measurement by GC-MS, $^1$H-NMR spectrometry, IR spectrophotometry and elementary analysis to obtain the results shown below.

GC-MS analysis: Parent ion peak, 335

NMR: δ (ppm): 0.67 (t, Si—CH$_2$, 2H), 1.26 (d, C—C—CH$_3$, 3H), 1.60 (m, N—CH$_2$, 2H), 3.10 (q, N—CH$_2$, 2H), 3.51 (s, O—CH$_3$, 9H), 4.15 (q,

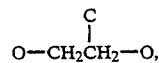

3H), 5.6–6.3 (m, CH=CH$_2$, 3H).

Figure 4:
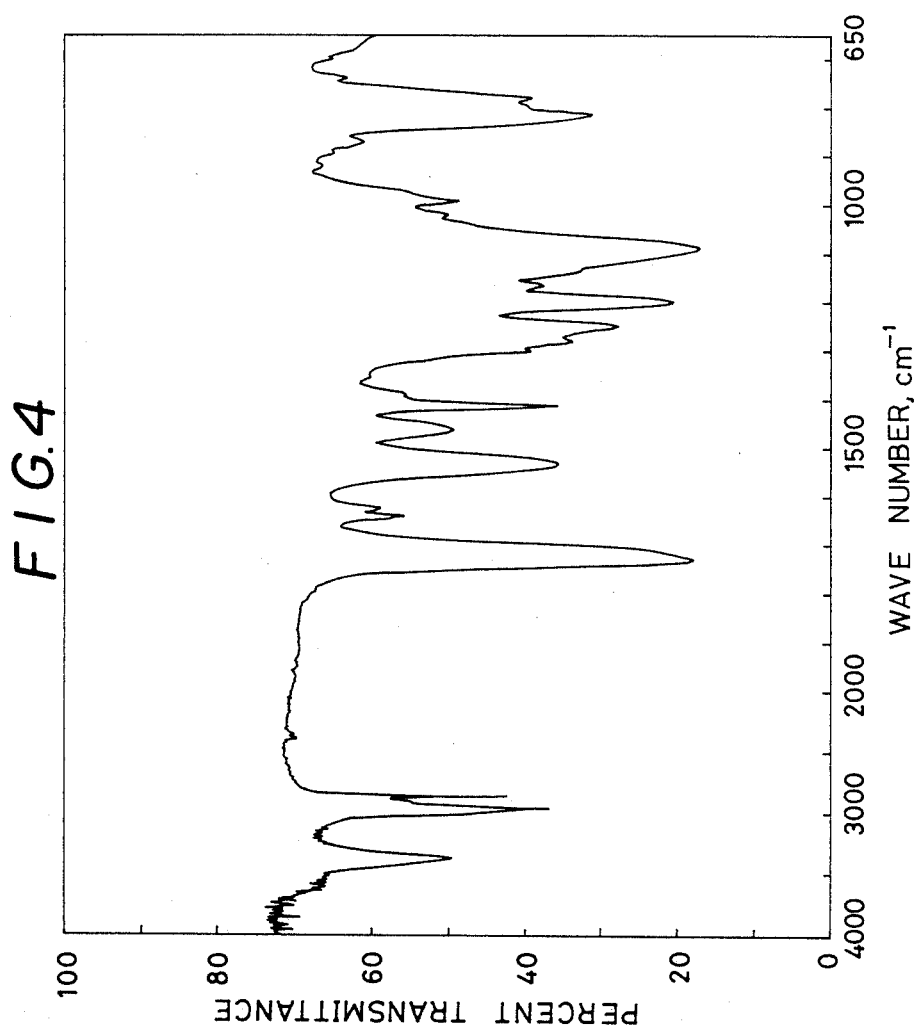

IR spectrum: As shown in FIG. 4. Characteristic absorption bands (cm$^{-1}$) 3350 (N—H); 1725 (C=O); 1636, 1620 (C=C).

| Elementary analysis: (%) | | | |
|---|---|---|---|
| | C | H | Si |
| Calculated: (as C$_{13}$H$_{24}$NSiO$_7$) | 46.6 | 7.5 | 8.4 |
| Found: | 46.6 | 7.4 | 8.3 |

From the foregoing results, the above product was identified to be a compound represented by the formula:

Yield: 73%.

Example 5

Example 1 was repeated except for using 8.6 g of 2-hydroxyisopropyl methacrylate in place of 2-hydroxyethyl acrylate, to obtain 116 mg (yield: 84%) of a liquid product having a refractive index $n_D^{25}$ of 1.4507.

Next, this compound was subjected to measurement by GC-MS, 1H NMR spectrometry, IR spectrophotometry and elementary analysis to obtain the results shown below.

GC-MS analysis: Parent ion peak, 349.

NMR: δ (ppm): 0.57 (t, Si—CH$_2$, 2H), 1.27 (d, C—C—CH$_3$, 3H), 1.61 (m, C—CH$_2$—C, 2H), 1.95 (s, C=C—CH$_3$, 3H), 3.11 (q, N—CH$_2$, 2H), 3.52 (s, O—CH$_3$, 9H), 4.09 (q,

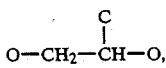

3H), 5.50, 6.04 (s, C=CH$_2$, 2H).

Figure 5:
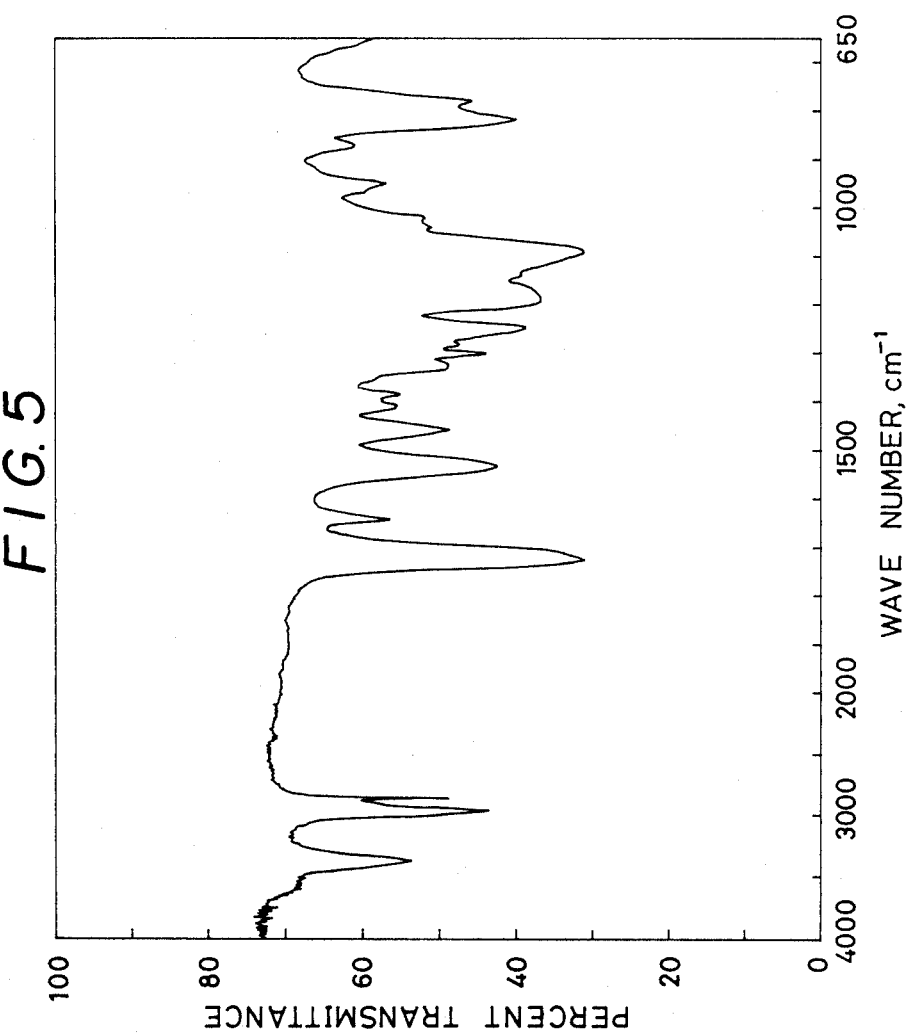

IR spectrum: As shown in FIG. 5. Characteristic absorption bands (cm$^{-1}$) 3350 (N—H); 1720 (C=O); 1637 (C=C).

| Elementary analysis: (%) | | | |
|---|---|---|---|
| | C | H | Si |
| Calculated: (as C$_{14}$H$_{26}$NSiO$_7$) | 48.1 | 7.8 | 8.0 |
| Found: | 47.9 | 7.6 | 8.2 |

From the foregoing results, the above product was identified to be a compound represented by the formula:

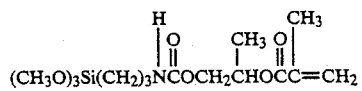

What is claimed is:

1. An organosilicon compound represented by the general formula (I):

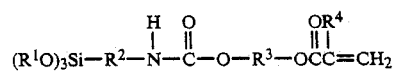

wherein R$^1$ may be the same or different and represents an alkyl group having 1 to 8 carbon atoms; R$^2$ and R$^3$ may be the same or different and represents an alkylene group having 1 to 8 carbon atoms; and R$^4$ represents a hydrogen atom or an alkyl group having 1 to 8 carbon atoms.

2. An organosilicon compound according to claim 1, wherein in the general formula (I) R$^1$ is a methyl group or ethyl group, R$^2$ and R$^3$ may be the same or different and are each an alkylene group having 2 to 4 carbon atoms, and R$^4$ is a hydrogen atom or a methyl group.

3. A process for preparing an organosilicon compound represented by the general formula (I):

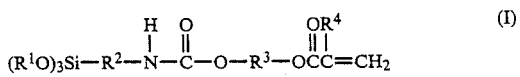

wherein R$^1$ may be the same or different and represents an alkyl group having 1 to 8 carbon atoms; R$^2$ and R$^3$ may be the same or different and represents an alkylene group having 1 to 8 carbon atoms; and R$^4$ represents a hydrogen atom or an alkyl group having 1 to 8 carbon atoms,
comprising reacting an organosilicon compound represented by the general fromula (II):

wherein R$^1$ and R$^2$ are as defined above;
with a compound represented by the general formula (III):

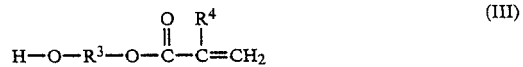

wherein R$^3$ and R$^4$ are as defined above;
in the presence of a catalyst.

4. A process according to claim 3, wherein in the general formulas (I), (II) and (III) R$^1$ is a methyl group or ethyl group, R$^2$ and R$^3$ may be the same or different and are each an alkylene group having 2 to 4 carbon atoms, and R$^4$ is a hydrogen atom or a methyl group.

5. A process according to claim 3, wherein said catalyst is selected from the group consisting of organic tin compounds and tert-amines.

6. A process according to claim 5, wherein said catalyst is selected from the group consisting of dibutyltin maleate, tributyltin acetate, dimethyltin dichloride, dibutyltin diacetate, dibutyltin dilaurate, N-methylmorpholine, triethylamine, N-methylpiperidine, N,N-dimethylcyclohexylamine and pyridine.

7. A process according to claim 5, wherein the reaction of the organosilicon compound of the general formula (II) with the compound of the general formula (III) is carried out in the absence of solvent.

8. A process according to claim 5, wherein the reaction of the organosilicon compound of the general formula (II) with the compound of the general formula (III) is carried out in solvent.

* * * * *